United States Patent [19]

Yasuo

[11] Patent Number: 5,352,894
[45] Date of Patent: Oct. 4, 1994

[54] ELECTRON SPECTROSCOPY ANALYZER AND A METHOD OF CORRECTING A SHIFT OF SPECTRAL LINE IN ELECTRON SPECTROSCOPY

[75] Inventor: Fumitoshi Yasuo, Ayama, Japan

[73] Assignee: Sharp Kabushiki Kaisha, Osaka, Japan

[21] Appl. No.: 123,047

[22] Filed: Sep. 20, 1993

[30] Foreign Application Priority Data

Oct. 19, 1992 [JP] Japan .................... 4-306536

[51] Int. Cl.$^5$ .................................. H01J 37/26
[52] U.S. Cl. ...................... 250/305; 250/310
[58] Field of Search ............ 250/305, 306, 307, 310

[56] References Cited

U.S. PATENT DOCUMENTS

| | | | |
|---|---|---|---|
| 3,631,238 | 12/1971 | MacDonald | 250/305 |
| 4,355,232 | 10/1982 | Todokoro et al. | 250/305 |
| 4,645,929 | 2/1987 | Criegern et al. | 250/307 |
| 4,680,467 | 7/1987 | Bryson, III et al. | 250/305 |
| 5,118,941 | 6/1992 | Larson | 250/305 |

FOREIGN PATENT DOCUMENTS

| | | |
|---|---|---|
| 0150326 | 8/1985 | European Pat. Off. . |
| 0200333 | 12/1986 | European Pat. Off. . |
| 57-119442 | 7/1982 | Japan . |
| 3-176957 | 7/1991 | Japan . |
| 4-138647 | 5/1992 | Japan . |

OTHER PUBLICATIONS

"Reduction of Charging in Surface Analysis of Insulators by AES", *Journal of Applied Physics Soc.*, Spring, 1989, 3p-L-7.

"Effects of Helium Ion Bombardment on Auger Electron Spectroscopy", *Journal of Applied Physics Soc.*, 1989, 28p-H-2.

"Effects of Helium Ion Bombardment on Auger Electron Spectroscopy (II)", *Journal of Applied Physics Soc.*, 1990, 28a-ZG-3.

*Primary Examiner*—Jack I. Berman
*Assistant Examiner*—James Beyer
*Attorney, Agent, or Firm*—Nixon & Vanderhye

[57] ABSTRACT

In an electron spectroscopy analyzer for obtaining an electron spectroscopy spectrum by applying to a sample an X-ray or electron beam from a first beam source and by analyzing the energy of secondary electrons emitted from the sample, an amount of energy shift of a reflected beam from the sample is obtained by applying a charging beam from second beam source, and a shift of the electron spectroscopy spectrum is corrected in accordance with the amount of energy shift. With this structure, a shift of a spectral line due to charges on the sample surface caused by the application of the X-ray or electron beam is corrected, thereby improving accuracy of the measurement of values and intensity of energy.

19 Claims, 7 Drawing Sheets

PEAK HEIGHT (INTENSITY) = $I_p - I_b$

FIG. 7 (b)

PEAK SHIFTS DEPENDING ON LOCATIONS ($P_1 - P_3$)

ELECTRON SPECTROSCOPY ANALYZER AND A METHOD OF CORRECTING A SHIFT OF SPECTRAL LINE IN ELECTRON SPECTROSCOPY

FIELD OF THE INVENTION

The present invention relates to an electron spectroscopy analyzer such as Auger electron spectroscopy and an X-ray photoelectron spectroscopy for analyzing elements. The present invention more particularly relates to an electron spectroscopy capable of correcting a shift of a spectral line caused by charges on a sample surface and to a method of correcting such a shift.

BACKGROUND OF THE INVENTION

For example, when a beam of electrons or X-rays is focused on a sample surface to analyze an element, secondary electrons such as excited Auger electrons or photoelectrons are emitted. The energy of these secondary electrons easily changes as the potential of the sample surface changes. Such changes in the potential of the sample surface are observed when the sample surface is charged by a beam of electrons from an excitation source or by an emission of secondary electrons. With a conventional method, changes in the potential on the sample surface are restrained by preventing the sample surface from being charged.

For example, the following methods are used to prevent the sample surface from being charged when a beam having charges is applied to the sample surface from the excitation source.

(1) Incident charges and emitted charges are caused to balance by varying the energy, incident angle and amount of current of a beam applied to the sample surface from the excitation source.

(2) Positive charges and negative charges on the sample surface are caused to balance by simultaneously applying to the sample a beam from the excitation source and a beam having a charge opposite to that of the beam from the excitation source.

(3) The amount of charges per unit area on the sample surface is reduced by decreasing the current density of the excitation source.

(4) If the sample has a multi-layer structure including an electrically conductive layer as a lower layer, the energy of the beam is increased to cause the beam from the excitation source to reach the electrically conductive layer, and the charges are emitted through the electrically conductive layer.

The sample surface is positively charged by the emission of the secondary electrons. Then, a beam (generally an electron beam) having opposite charges is applied to the sample surface so as to cause the positive charges and the negative charges on the sample surface to balance.

However, these methods have the following drawbacks.

These methods are the method of balancing the incident charges and emitted charges, and the method of reducing the amount of charges. They are thus useful to reduce the charges on the sample surface to a level which makes a measurement unavailable. However, they cannot completely prevent a slight change in the potential of the sample surface during the analysis. Namely, they cannot fully prevent a shift of spectral line caused by a slight change in the potential of the sample surface with the passage of time.

For example, with an electron spectroscopy in which the S/N ratio is improved by the addition of data, when a shift of spectral line is caused (see FIG. 5($a$)) by the passage of time during the analysis, the analytical spectrum obtained by the addition of data has a broader peak as shown in FIG. 5($b$). The spectrum having the peak shown in FIG. 5($d$) is expected to be obtained by the addition of the analytical spectra obtained at time $t_0$, $t_1$ (or $t_0+\Delta t$), and $t_2$ (or $t_1+\Delta t$) shown in FIG. 5($c$). However, when a shift of the spectral line occurs with the passage of time as shown in FIG. 5($a$), the peak becomes broader as shown in FIG. 5($b$). Namely, when the peak becomes broader due to such a shift, the energy resolution and the accuracy of determination are lowered.

When sputter etching is used for the electron spectroscopy, not only the surface of a sample but also the depth profile thereof is analyzed. In this case, if the sample is a thin film or has a multi-layer structure, the film thickness of the topmost thin film and the constituent elements/composition of the topmost layer change as the sputter etching proceeds. Thus, the amount of charge on the sample surface changes and a shift of a spectral line occurs.

Figures 6A, 6B:
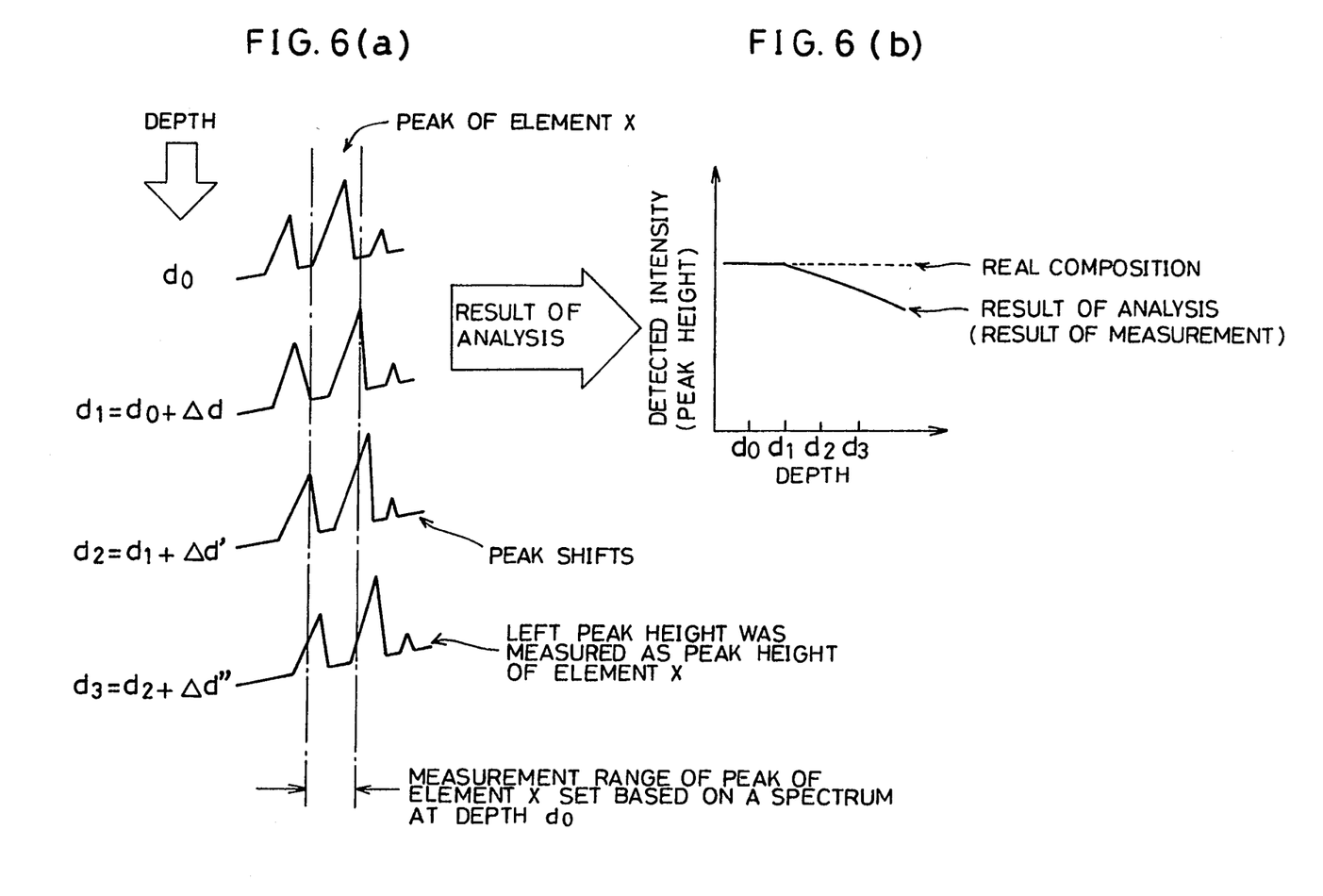
FIG. 6(a) is a graph showing analytical spectra as a function of depth below a surface profile where a shift of a spectral line occurs when analyzing a depth profile of an element.
FIG. 6(b) is a graph showing a difference between the result of analysis and the real composition of the element.

As shown in FIG. 6($a$), when a shift of the spectral line occurs depending on a depth of the sample below the surface, the target peak appears outside of a measurement range of a peak or a peak other than the target peak appears within the measurement range. Namely, when detecting a peak of element X, even if the peak of the element X occurs within the measurement range at a depth $d_0$ and a depth $d_1$ (or $d_0+\Delta d$), the peak emerges outside the measurement range at a depth $d_2$ (or $d_1+\Delta d'$) and a depth $d_3$ (or $d_2+\Delta d''$). At the depth $d_3$, since a peak of an element other than element X appears within the measurement range, the peak of the element other than the element X is measured as a peak of the element X. Therefore, as shown in FIG. 6($b$), there is a difference between the apparent composition of the element obtained from the result of analysis and the real composition of the element, preventing accurate analysis.

Figure 7:
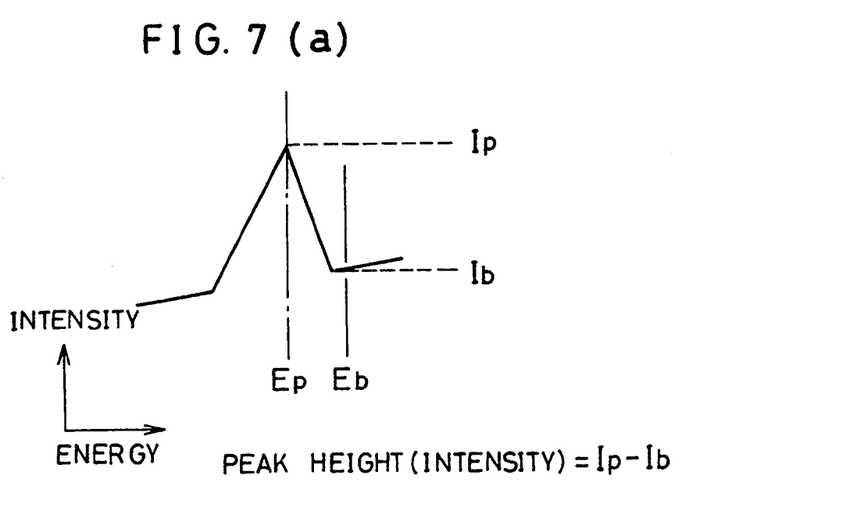
FIG. 7(a) is a view explaining a method of measuring a detected intensity in the elementary mapping analysis.
FIG. 7(b) is a graph showing analytical spectra at measurement points where a shift of a spectral line occurs during the elementary mapping analysis.

Moreover, in the elementary mapping analysis using electron spectroscopy, generally, a mapping area is divided into 128×128 pixels, for example, and a peak height of the target element of mapping is measured in each pixel. As the number of pixels is great, the peak height in each pixel is measured by detecting intensities of a point $E_p$ of the peak top $I_p$ and one or two points $E_b$ of the background $I_b$ and by obtaining a difference ($I_p$—$I_b$) as shown in FIG. 7($a$).

In the elementary mapping analysis, if the sample surface has areas of different conductivities, the amount of charge on the sample surface varies depending on locations. Consequently, the shift of spectral line varies depending on locations ($P_1$ to $P_3$) of the sample surface. In this case, as shown in FIG. 7($b$), the measured peak height is erroneous, preventing accurate mapping analysis.

SUMMARY OF THE INVENTION

It is an object of the present invention to provide an electron spectroscopy analyzer capable of correcting a shift of a spectral line due to charges on a sample surface caused by the application of a charging beam from a beam source.

In order to achieve the above object, an electron spectroscopy analyzer of the present invention includes at least:

(1) a first beam source for causing a sample to emit analytical secondary electrons by applying a main beam to the sample;
(2) spectrum detecting means for detecting an electron spectroscopy spectrum by analyzing an energy of the analytical secondary electrons;
(3) a second beam source for applying to the sample a charging beam having an energy lower than an energy of the main beam; and
(4) shift detecting means for detecting an amount of an energy shift of a reflected beam produced by applying the charging beam to the sample.

With this structure, an amount of shift of the energy of the reflected beam is detected by the shift detecting means by applying the charging beam from the second beam source to the sample. The charges on the sample surface due to the application of the main beam cause a shift of spectral line in the electron spectroscopy spectrum detected by the spectrum detecting means.

However, the shift of the spectral line is corrected in accordance with the amount of shift of energy detected by the shift detecting means. The energy and current of the charging beam are set so that a peak of a reflected beam produced by the application of the charging beam from the second beam source to the sample has an intensity similar to that of a peak of an element to be analyzed and appears in the vicinity of the peak of the element in an analytical spectrum obtained by the application of the main beam from the first beam source. In this case, an amount of shift of the analytical spectrum (peak) is obtained by examining the energy of the reflected beam. When the charging beam from the second beam source is applied to the sample, secondary electrons are emitted in a manner similar to the application of the main beam. However, the intensity of the secondary electrons is considerably lower than that of the reflected beam. Namely, when the energy and current of the charging beam from the second beam source are set as described above, a peak obtained by the charging beam is ignored as it is lower than the peak in the analytical spectrum of the main beam and only the peak of the reflected beam is detected.

Therefore, when a sample material having changeable surface potential such as an insulating material is analyzed a plurality of times and when the results are added up so as to have an improved S/N ratio, even if a shift of spectral line occurs with the passage of time, the values and intensity of energy are measured with accuracy by correcting the shift in accordance with the detected amount of shift of energy.

When a depth profile of the sample with multi-layer structure is measured by using sputter etching, a shift of spectral line occurs as the constituent elements/composition of the topmost layer or its thickness changes. However, even in this case, it is possible to prevent a peak other than the target peak from appearing within the measurement range of the target peak by detecting the amount of shift as a function of depth below the surface and correcting the shift of the spectral line. Since the results of analysis of elements whose peaks appear adjacent each other in the spectra are clearly distinguished from each other, the accuracy of analysis is improved.

Moreover, in the elementary mapping analysis of a sample having areas with electrically different structures in the surface and potential varying depending on locations on the surface, the amount of a shift is measured at each location. It is therefore possible to suitably correct the shift at each location and to analyze elements with accuracy.

For a fuller understanding of the nature and advantages of the invention, reference should be made to the ensuing detailed description taken in conjunction with the accompanying drawings.

DESCRIPTION OF THE PREFERRED EMBODIMENTS

Figure 1:
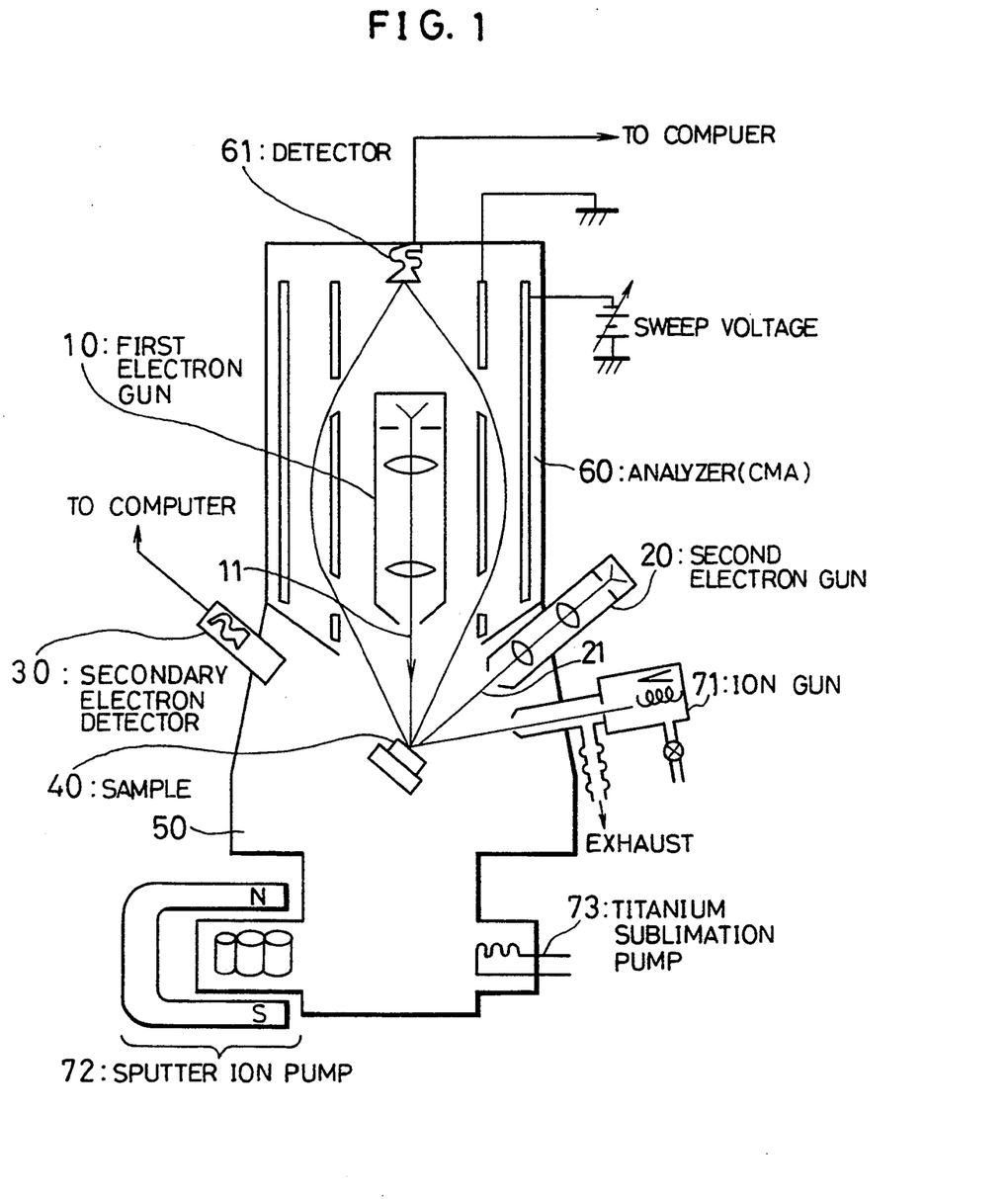
FIG. 1 is a depiction illustrating one of the possible structures of an electron spectroscopy analyzer of the present invention.

FIG. 1 illustrates a schematic structure of an electron spectroscopy analyzer according to one embodiment of the present invention.

The electron spectroscopy analyzer of this embodiment is capable of correcting a shift of a spectral line, and has a container 50 including therein a first electron gun 10 as a first beam source and a second electron gun 20 as a second beam source. The container 50 also includes therein a CMA (cylindrical mirror analyzer) 60 and a detector 61. The CMA 60 analyzes the energy of Auger electrons (analytical secondary electrons) emitted from a sample 40 when an electron beam (a main beam) 11 from the first electron gun 10 impinges on the sample 40. After the energy of the Auger electrons has been analyzed, the detector 61 detects the Auger electrons. The CMA 60, the detector 61 and a computer, not shown, connected to the detector 61 together form spectrum detecting means in the electron spectroscopy analyzer.

The reflected electron (reflected beam) emitted from the sample 40 upon the application of an electron beam (charging beam) 21 from the second electron gun 20 are detected by the CMA 60 and the detector 61. Shift detecting means in the electron spectroscopy analyzer is formed by the CMA 60, the detector 61, and a computer connected to the detector 61. The computer functions as correcting means.

The container 50 is provided with a secondary electron detector 30 for detecting secondary electrons produced by the electron beam applied to the sample 40 from the first electron gun 10 and the second electron gun 20. The computer is also connected to the secondary electron detector 30. A location on the sample surface to be observed or analyzed is specified using the computer and the secondary electron detector 30. The computer and the secondary electron detector 30 form controlling means for controlling the electron beams 11 and 21 to be applied to the same position.

The sample 40 is disposed in the container 50 by a sample introducing system, not shown, and suitably moved by a stage driving system, not shown.

A shift of a spectral line in the surface analysis of the sample 40 is corrected as follows.

Figure 2A:
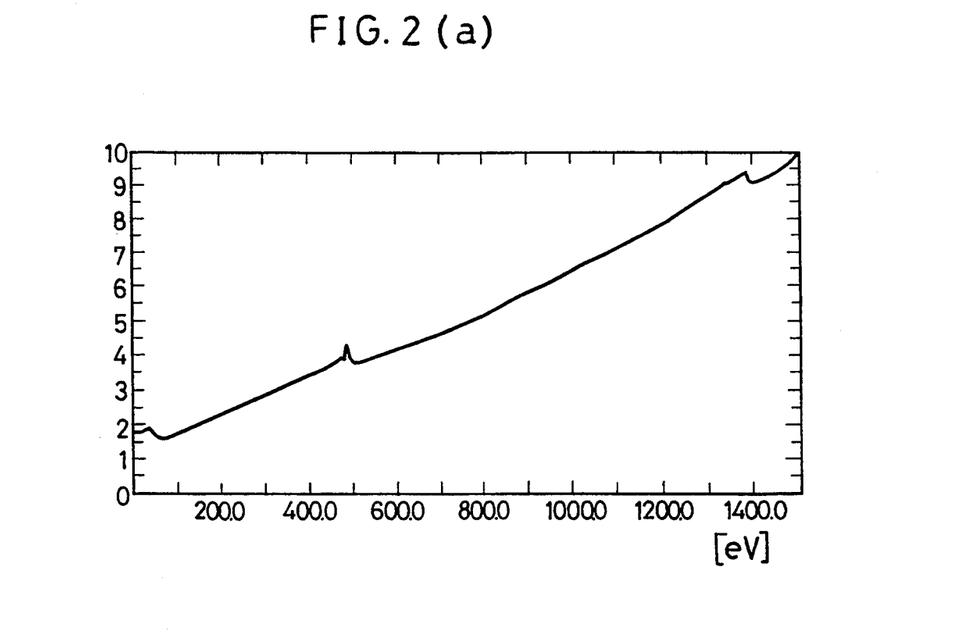
FIG. 2(a) is a graph showing an integral waveform of Auger electron spectroscopy spectrum produced by a first electron gun.

When the electron beam 11 from the first electron gun 10 strikes the sample 40, Auger electrons are emitted from the sample 40. The energy of the Auger electrons is analyzed by the CMA 60. Then, the Auger electrons are detected by the detector 61. The Auger electron spectroscopy spectra shown in FIGS. 2(a) and 2(b) are obtained by the computer connected to the detector 61.

Figure 2B:
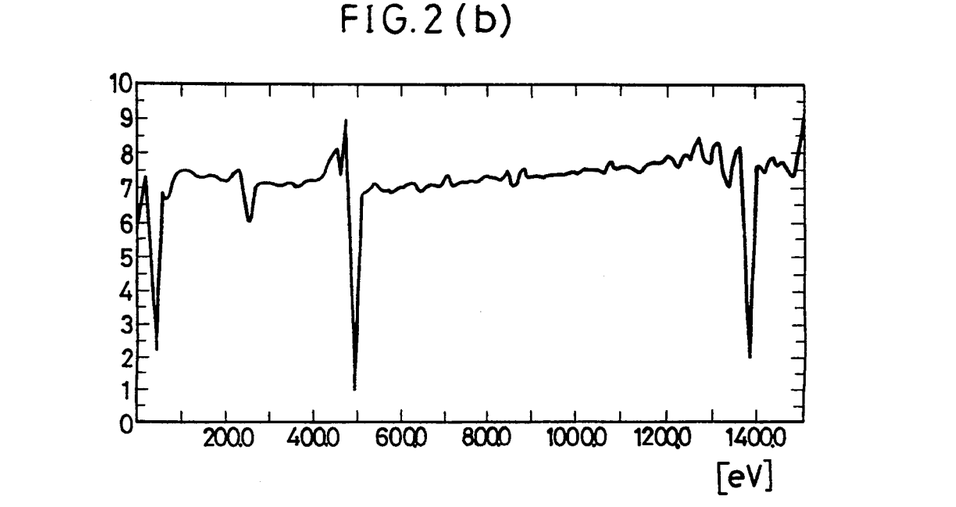
FIG. 2(b) is a graph showing a differential waveform of the Auger electron spectroscopy spectrum.

In the Auger electron spectroscopy spectrum shown in FIG. 2(b), peaks of the Al element are seen around 70 eV and 1400 eV, a peak of the C element is seen around 270 eV, and a peak of the O element is seen around 500 eV.

Figure 3A:
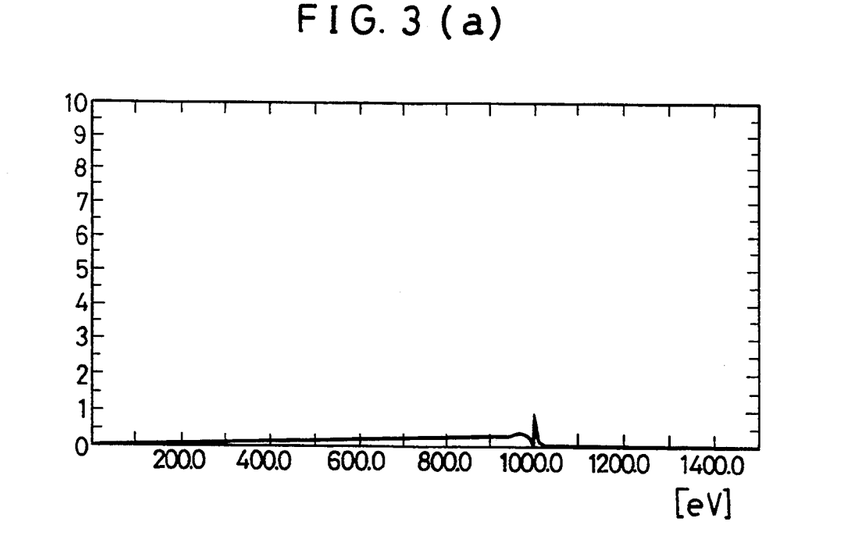
FIG. 3(a) is a graph showing an integral waveform of electron spectroscopy spectrum produced by a second electron gun.

The electron beam 21 from the second electron gun 20 is focused on a position of the sample 40 where the electron beam 11 was focused. The energy of reflected electrons emitted from the sample 40 by the application of the electron beam 21 to the sample 40 and of the secondary electrons produced by the application of the electron beam 11 are analyzed by the CMA 60 and detected by the detector 61. The electron spectroscopy spectra shown in FIGS. 3(a) and 3(b) are given by the computer connected to the detector 61.

Figure 3B:
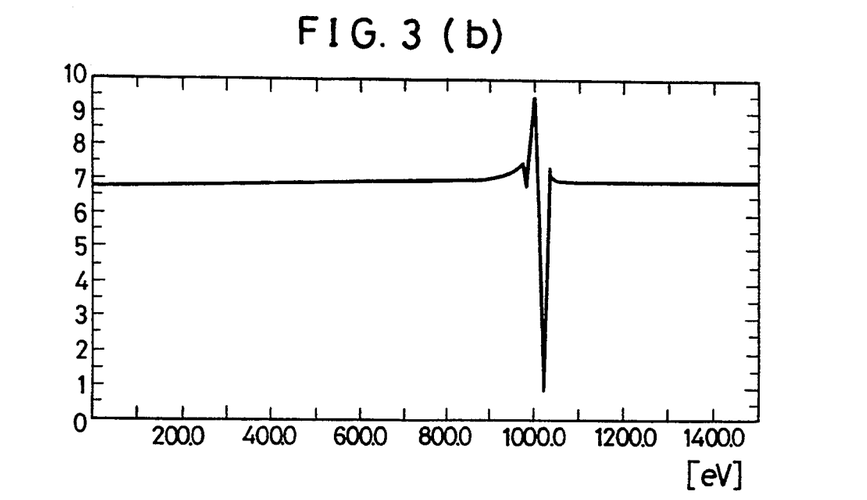
FIG. 3(b) is a graph showing a differential waveform of the electron spectroscopy spectrum.

In the electron spectroscopy spectrum shown in FIG. 3(b), a peak of the reflected electrons is seen around 1000 eV. The accelerating energy of the second electron gun 20 appears as the peak of the reflected electrons in the spectrum. The accelerating energy of the second electron gun 20 is set so that the peak of the reflected electrons occurs at a position which is close to but not superimposed on the position where the peak of the Auger electrons of an element constituting the sample 40 occurs.

The beam current of the second electron gun 20 has a value lower than that of the first electron gun 10. With this arrangement, when the electron beam 11 from the first electron bun 10 and the electron beam 21 from the second electron gun 20 are applied at the same time, the peak of the Auger electron produced by the electron beam 21 does not interfere with the peak of the Auger electron produced by the electron beam 11.

The beam current of the second electron gun 20 is set not greater than about 1/1000 of the beam current of the first electron gun 10 in accordance with the detection limit of the detector 61. The peak intensity of the reflected electrons is more than ten times of the peak intensity of the Auger electrons. Therefore, even when the beam current of the electron beam 21 is set lower than about 1/1000 of the beam current of the electron beam 11, the reflected electrons are detectable.

Figure 4:
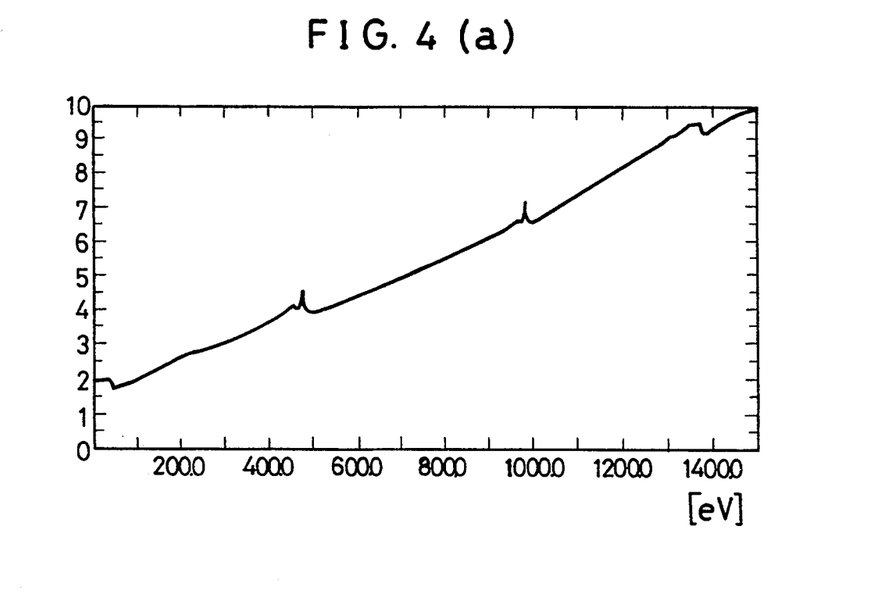
FIG. 4(a) is a graph showing an integral waveform of Auger electron spectroscopy spectrum produced by the first and second electron guns.
FIG. 4(b) is a graph showing a differential waveform of the Auger electron spectroscopy spectrum.
Figure 5A:
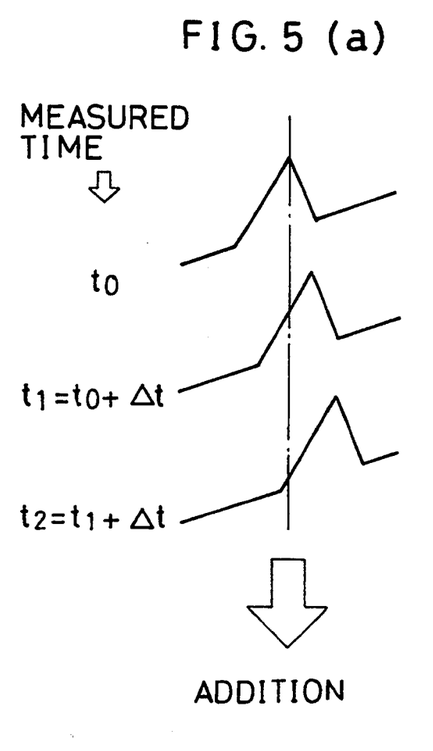
FIG. 5(a) is a graph showing analytical spectra at times where a sift of a spectral line occurs.
Figure 5B:
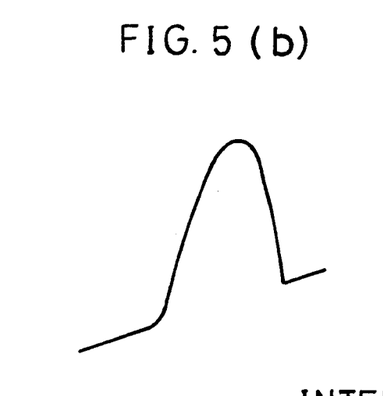
FIG. 5(b) is a graph showing a peak obtained by adding the analytical spectra of FIG. 5(a)
Figure 5C:
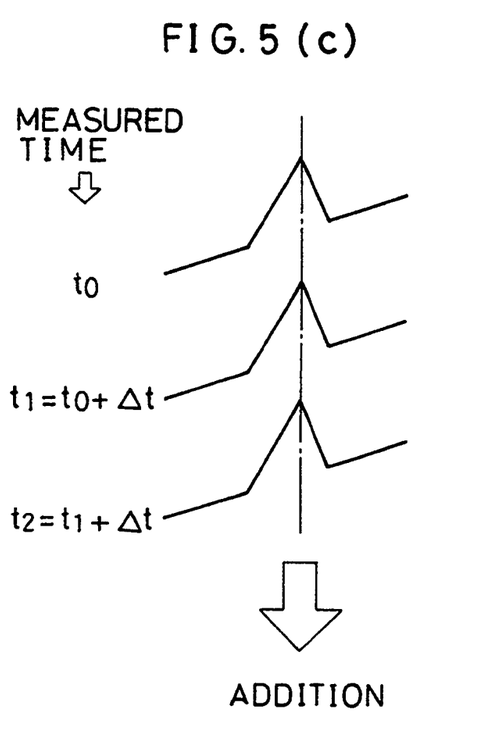
FIG. 5(c) is a graph showing analytical spectra at times where a spectral line does not shift.
Figure 5D:
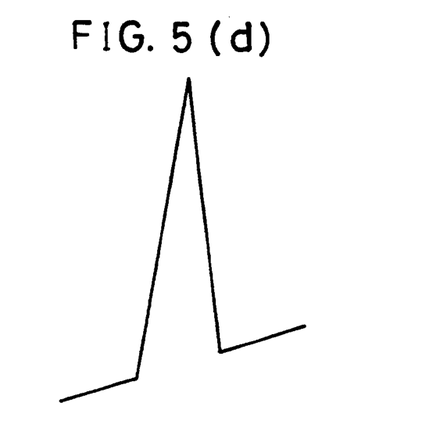
FIG. 5(d) is a graph showing a peak obtained by adding the analytical spectra of FIG. 5(c).

When the electron beam 11 from the first electron gun 10 and the electron beam 21 from the second electron gun 20 strike the sample 40 at the same time, the computer connected to the detector 61 gives the Auger electron spectroscopy spectra shown in FIGS. 4(a) and 4(b) as the sum of the electron spectroscopy spectra obtained by the application of the electron beams 11 and 21 from the electron guns 10 and 20 to the sample 40.

When the Anger electron spectroscopy spectrum is obtained by adding analytical data, a shift of the energy (peak value) of the reflected electrons produced by the application of the electron beam 21 from the second electron gun 20 to the sample 40 is monitored every n (n is a positive integral number) times. The amount of the energy of the reflected electrons is taken as the amount of shift of the spectrum on the whole, and the spectrum is corrected by the amount of the shift. Then, all the analytical data is added.

Therefore, even when an element whose surface potential is changeable, such as an insulating matter, is analyzed, a shift of the spectrum line which occurs with the passage of time is adjustable, improving the accuracy of measuring the energy values and intensity.

When analyzing a depth profile by using an ion gun 71, a sputter ion pump 72 and a titanium sublimation pump 73 in the container 50 and by performing sputter-etching, if the sample 40 is a thin-film or has a multi-layer structure, the film thickness of the top layer and the constituent elements/composition of the top layer change as the sputter-etching proceeds. This causes a change in the amount of charge on the sample surface, resulting in a shift of a spectral line. Namely, an accurate depth profile cannot be obtained by supper-etching.

The following description discusses a method of correcting a shift of a spectral line used in the analysis of a depth profile by sputter-etching.

A depth profile is generally obtained by in turn performing spectral analysis and sputter-etching. In spectral analysis, similar to the method of correcting a shift of a spectral line used for the surface analysis, a shift of the energy of the reflected electrons of the second electron gun 20 is periodically monitored. The shifts of the spectral line are corrected according to the shift monitored.

This arrangement enables the shift of the spectral line caused by a change in the depth to be corrected. It is therefore possible to prevent a peak other than a target peak from occurring within a measurement range of the target peak. Thus, the results of analysis of elements whose peaks occur at adjacent positions in the spectrum are clearly distinguished from each other, improving the accuracy of the analysis.

In the mapping analysis using Auger electron spectroscopy, the measuring field is divided into pixels of $L \times M$ (both L and M are positive integral), and the peak intensity of a specified element is measured in each pixel. If there are areas having different electric conductivities in the sample surface, the amount of charge on the sample surface varies depending on locations. This causes the amount of the shift of a spectral line to vary depending on a measured point. As a result, errors occur in the measured value of the peak height. Namely, accurate mapping analysis is not performed.

Then, in the elementary mapping analysis, the shift of the spectral line is corrected as follows.

A secondary electron image of an area subjected to the elementary mapping analysis is produced by the electron beam 11 from the first electron gun 10.

Next, the secondary electron image formed by the electron beam 21 from the electron gun 20 is compared with the secondary electron image formed by the electron beam 11 from the electron gun 10 so as to cause the electron beams 11 and 21 to strike the same area. At this time, the accelerating energy and the beam current of the electron beam 21 are determined to meet the standard set for the method of correcting a shift of a spectral line in the surface analysis.

When the electron beams 11 and 21 strike the same area, they are scanned in a synchronous manner to perform mapping analysis. At this time, an energy shift of the reflected electrons of the electron beam 21 is measured in each pixel. An energy value $E_p$ of the peak top and an energy value $E_b$ of the background are corrected according to the results of the measurement. Then, the intensities ($I_p$ and $I_b$) of electrons having such energy values are measured to obtain a peak height (intensity $= I_p - I_b$).

Even when areas in the surface of the sample 40 have electrically different structures, a shift of a spectral line is corrected according to a measured point. Thus, the distribution of elements is accurately measured.

As described above, a shift of a spectral line is suitably corrected by detecting an amount of the shift with the second electron gun 20 and the detector 61 when adding the spectra obtained by a plurality of measurements, when analyzing a depth profile, and when performing the elementary mapping analysis. It is therefore possible to obtain accurate measurement results.

In this embodiment, the Auger electron spectroscopy using an electron beam is explained. However, the present invention is also applicable to an elemental analysis using X-rays instead of the electron beam.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An electron spectroscopy analyzer comprising:
   a first beam source for causing a sample to emit analytical secondary electrons by applying a main beam to said sample;
   spectrum detecting means for detecting an electron spectroscopy spectrum by analyzing an energy of said analytical secondary electrons;
   a second beam source for applying to said sample a charging beam having an energy lower than an energy of said main beam; and
   shift detecting means for detecting an amount of an energy shift of a reflected beam produced by said charging beam.

2. The electron spectroscopy analyzer according to claim 1, further comprising correcting means for correcting said electron spectroscopy spectrum in accordance with the amount of the energy shift.

3. The electron spectroscopy analyzer according to claim 1,
   wherein an accelerating energy of said second beam source is set so that a peak of the spectrum produced by said reflected beam and a peak of the spectrum produced by said analytical secondary electrons occur at different locations.

4. The electron spectroscopy analyzer according to claim 1,
   wherein a beam current of said charging beam is smaller than a beam current of said main beam.

5. The electron spectroscopy analyzer according to claim 1,
   wherein said main beam is an electron beam.

6. The electron spectroscopy analyzer according to claim 1,
   wherein said main beam is an X-ray beam.

7. The electron spectroscopy analyzer according to claim 1,
   wherein said charging beam is an electron beam.

8. The electron spectroscopy analyzer according to claim 1,
   wherein said analytical secondary electrons are Auger electrons.

9. The electron spectroscopy analyzer according to claim 1,
   wherein said analytical secondary electrons are photoelectrons.

10. The electron spectroscopy analyzer according to claim 1, further comprising ion-beam generating means for applying an ion beam to said sample for sputter etching.

11. A method of correcting a shift of a spectral line in electron spectroscopy comprising the steps of:
   (1) detecting an amount of an energy shift of a reflected beam from a sample when a charging beam is applied to said sample; and
   (2) correcting a shift of a spectral line in electron spectroscopy of analytical secondary electrons emitted from said sample when a main beam is applied to said sample, in accordance with the amount of the energy shift.

12. The method of correcting a shift of a spectral line in electron spectroscopy according to claim 11,
   wherein said main beam is an electron beam.

13. The method of correcting a shift of a spectral line in electron spectroscopy according to claim 11,
   wherein said main beam is an X-ray beam.

14. The method of correcting a shift of a spectral line in electron spectroscopy according to claim 11,
   wherein said charging beam is an electron beam.

15. The method of correcting a shift of a spectral line in electron spectroscopy according to claim 11,
   wherein said analytical secondary electrons are Auger electrons.

16. The method of correcting a shift of a spectral line in electron spectroscopy according to claim 11,
   wherein said analytical secondary electrons are photoelectrons.

17. The method of correcting a shift of a spectral line in electron spectroscopy according to claim 11, further comprising the step of
   (3) sputter-etching said sample.

18. The method of correcting a shift of a spectral line in electron spectroscopy according to claim 17,
   wherein said first and second steps and said third step are alternately performed.

19. The method of correcting a shift of a spectral line in electron spectroscopy according to claim 11, further comprising the step of dividing a measuring field of a sample surface into a plurality of pixels,
   wherein said first and second steps are performed in each pixel.

* * * * *